United States Patent
Yamaguchi et al.

(10) Patent No.: US 7,352,900 B2
(45) Date of Patent: Apr. 1, 2008

(54) APPARATUS AND METHOD FOR PROCESSING PARTICLE IMAGES AND PROGRAM PRODUCT FOR SAME

(75) Inventors: Keiichi Yamaguchi, Kobe (JP); Hideo Kusuzawa, Kobe (JP); Kouhei Shiba, Kobe (JP)

(73) Assignee: Sysmex Corporation, Kobe (JP)

( * ) Notice: Subject to any disclaimer, the term of this patent is extended or adjusted under 35 U.S.C. 154(b) by 506 days.

(21) Appl. No.: 10/966,122

(22) Filed: Oct. 15, 2004

(65) Prior Publication Data

US 2005/0089191 A1  Apr. 28, 2005

(30) Foreign Application Priority Data

Oct. 22, 2003 (JP) .............................. 2003-361975
Oct. 22, 2003 (JP) .............................. 2003-361980

(51) Int. Cl.
G06K 9/48 (2006.01)
G06K 9/46 (2006.01)
G06K 9/52 (2006.01)

(52) U.S. Cl. .................... 382/192; 382/199; 382/203; 382/204; 382/206; 382/286

(58) Field of Classification Search ............... 382/192, 382/193, 199, 203, 204, 206, 286, 291; 250/573; 356/335

See application file for complete search history.

(56) References Cited

U.S. PATENT DOCUMENTS

| 5,166,537 | A  | * | 11/1992 | Horiuchi et al. ............ 250/573 |
| 5,721,433 | A  |   | 2/1998  | Kosaka |
| 6,246,786 | B1 | * | 6/2001  | Nishikiori et al. .......... 382/134 |
| 6,522,781 | B1 | * | 2/2003  | Norikane et al. ........... 382/203 |
| 6,546,352 | B2 | * | 4/2003  | Jahn .......................... 702/128 |
| 6,662,117 | B2 | * | 12/2003 | Naito ......................... 702/29 |

\* cited by examiner

Primary Examiner—Bhavesh M Mehta
Assistant Examiner—John B Strege
(74) Attorney, Agent, or Firm—Brinks Hofer Gilson & Lione

(57) ABSTRACT

A method for processing particle images are described that include: receiving image information obtained by capturing an image of a particle; determining the circumferential length and number of inflection points in the contour of a particle image based on the received image information; and calculating the degree of irregularity of the particle based on the determined circumferential length and number of inflection points.

12 Claims, 8 Drawing Sheets

APPARATUS AND METHOD FOR PROCESSING PARTICLE IMAGES AND PROGRAM PRODUCT FOR SAME

This application claims priority under 35 U.S.C. § 119 to Japanese Patent Application Nos. 2003-361975 and 2003-361980 both filed Oct. 22, 2003, the entire contents of which are hereby incorporated herein by reference.

FIELD OF INVENTION

The present invention relates to a method for processing particle images to determine information relating to the particles by acquiring images of particles and subjecting the particle images to image processing.

BACKGROUND

An example of the prior art of the present invention is a known particle image analyzer which includes a flow cell for converting a particle suspension flow into a flow surrounded by a sheath fluid, light irradiating means for irradiating the converted suspension flow with light, image sensing means for acquiring an image of the irradiated particles, image analyzing means for analyzing the acquired particle images, and a display means, wherein the image analyzing means includes a calculation means for measuring particle data relating to the surface area and circumferential length of each acquired particle image and calculating the circularity of the particle from the particle data, graph preparation means for preparing a histogram based on the particle diameter and particle frequency data and preparing a two-dimensional scattergram using two parameters corresponding to particle diameter and circularity for displaying on the display means, memory means for storing each acquired particle image, and a particle image recall means for collectively displaying particle images stored in the memory means on the display means (refer to U.S. Pat. No. 5,721,433).

Analyzing and measuring various kinds of information relating to particles has become increasingly important in recent years in manufacturing processes and quality management processes for various particle materials, such as fine ceramic particles, toners, pigments, cosmetic powders, food additives, and chemical agents.

Although particle shape and circularity or degree of agglutination and the like can be determined using conventional methods and apparatuses, other particle information, such as, for example, degree of particle irregularity and light attenuation rate cannot be determined.

BRIEF SUMMARY

In view of the above information, the present invention provides an apparatus and method for analyzing particle images capable of calculating the degree of irregularity and light attenuation rate of particles from obtained particle images.

A method for processing particle images of a first aspect of the present invention includes the steps of: (a) receiving image information obtained by capturing an image of a particle; (b) determining the circumferential length and number of inflection points in the contour of a particle image based on the received image information; and (c) calculating the degree of irregularity of the particle based on the determined circumferential length and number of inflection points.

A particle image processing apparatus of a second aspect of the present invention includes: (a) an image information receiving means for receiving image information obtained by capturing an image of a particle; and (b) an analyzing means for determining a circumferential length and number of inflection points of a particle image based on the received image information and determining the degree of irregularity of a particle based on the determined circumferential length and number of inflection points.

A particle image analyzing apparatus of a third aspect of the present invention includes: (a) a flow cell for forming a suspension fluid flow containing particles; (b) a light source for irradiating the suspension flow with light; (c) an image sensing unit for capturing an image of a particle irradiated by light and generating image information; and (d) an analyzing means for generating image data based on the image information, and calculating the degree of irregularity of the particle based on the circumferential length and number of inflection points of the contour of the particle image in the image data.

A computer-executable particle image processing program product of a fourth aspect of the present invention includes the steps of: (a) receiving image information obtained by capturing a particle image; (b) determining the circumferential length and number of inflection points of the contour of a particle image based on the received image information; and (c) calculating the degree of irregularity of a particle based on the circumferential length and number of inflection points of the contour of a determined particle image.

A method for particle image processing of a fifth aspect of the present invention includes the steps of: (a) receiving image information of a particle image and its background image obtained by capturing an image of a particle; (b) calculating an average value Ip of the luminance of pixels of the particle image and an average value Ib of the luminance of pixels of the background image using the received image information;, and (c) a step of determining the light attenuation rate $\alpha$ of a particle image based on the calculated values Ip and Ib.

A particle image processing apparatus of a sixth aspect of the present invention includes; (a) an image information receiving means for receiving image information including a background image and particle image obtained by capturing an image of a particle; (b) a first calculating unit for calculating the average value Ip of the luminance of pixels of a particle image using the received image information; (c) a second calculating unit for calculating an average value Ib of the luminance of pixels of a background image using the received image information; and (d) a third calculating unit for calculating the light attenuation rate $\alpha$ of a particle image based on the values Ip and Ib.

A computer-executable particle image processing program product of an seventh aspect of the present invention includes the steps of: (a) receiving image information of a particle image and its background image obtained by capturing an image of a particle; (b) calculating an average value Ip of the luminance of pixels of the particle image using the received image information; (c) calculating an average value Ib of the luminance of pixels of the background image using the received image information; and (d) determining the light attenuation rate $\alpha$ of a particle image based on the calculated values Ip and Ib.

DETAILED DESCRIPTION OF THE DRAWINGS AND THE PRESENTLY PREFERRED EMBODIMENTS

First Embodiment

Figure 1:
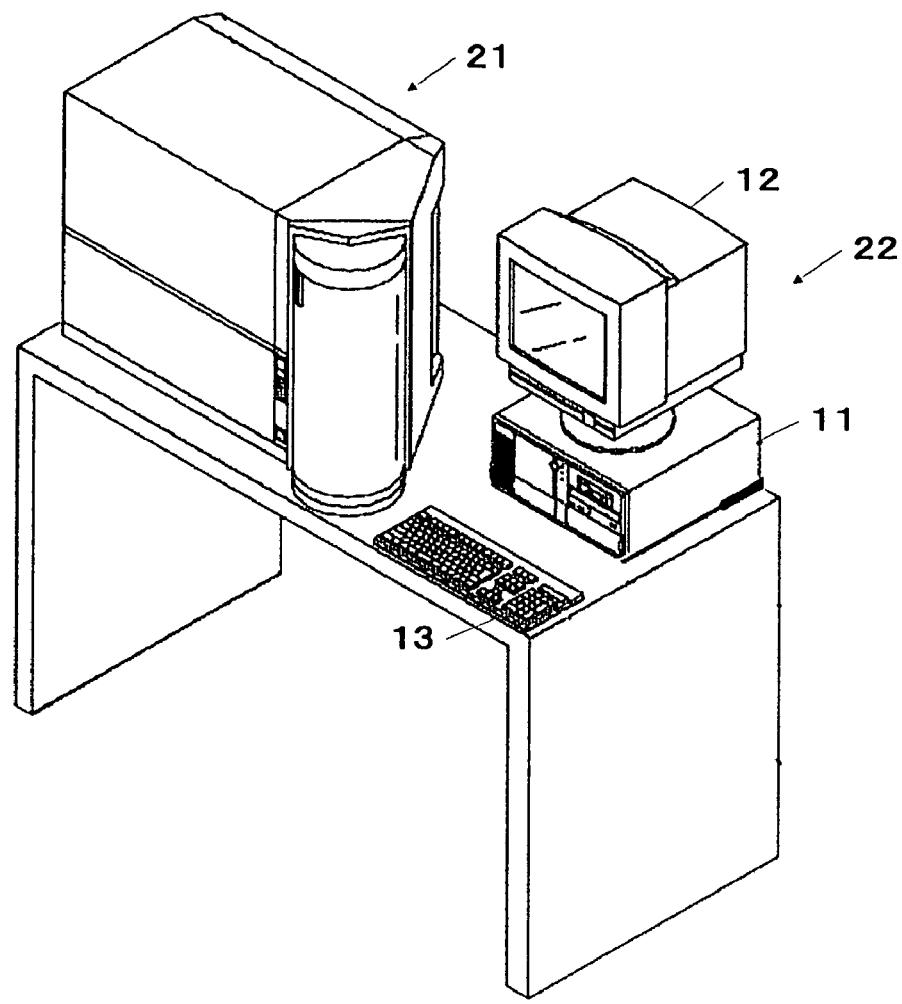
FIG. 1 is an exterior view of a first embodiment of a particle image analyzer.

An exterior view of a first embodiment of a particle image analyzer of the present invention is shown in FIG. 1. As shown in FIG. 1, the particle image analyzer includes a particle image sensing apparatus 21 and a data analyzer 22. The particle image sensing apparatus 21 and the data analyzer 22 are connected by a communication cable, such that an image captured in the particle image sensing apparatus 21 can be transmitted to the data analyzer 22 through the communication cable.

The data analyzer 22 includes a particle image processing device 11 for processing of images transmitted from the particle image sensing apparatus 21, television monitor 12 for displaying particle images and analysis data output from the particle image processing device 11, keyboard 13 for performing operations and data input to the particle image processing device 11, and a program reading unit 15 (refer to FIG. 4) for reading programs operating on the image processing device 11.

Figure 2:
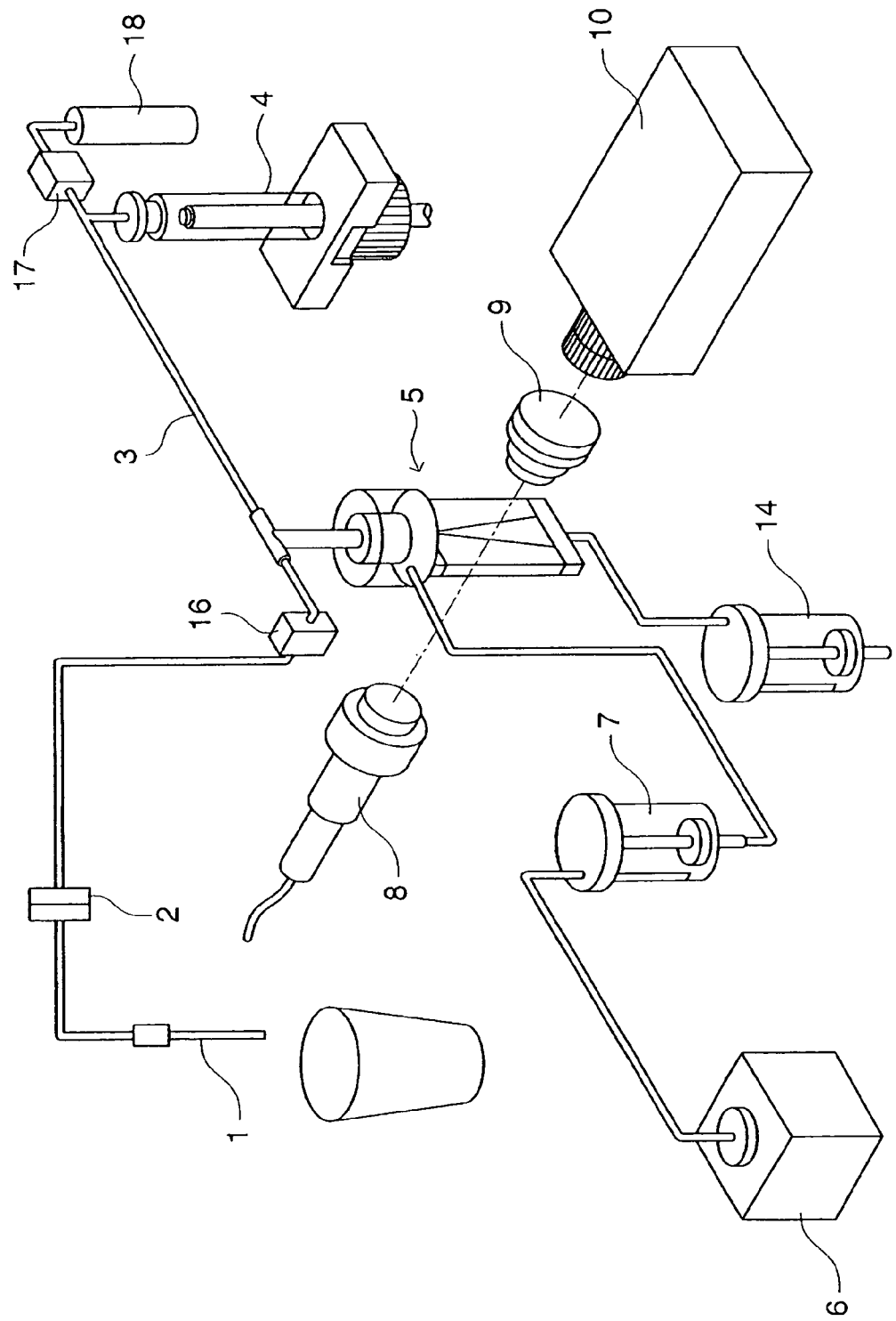
FIG. 2 illustrates an essential structure of a particle image sensing apparatus of the first embodiment.

The structure of the image sensing unit of the particle image sensing apparatus 21 is described below using FIG. 2. A suction pipette 1 is connected to a pump 18 through a sample filter 2, valve 16 and valve 17, as shown in FIG. 2. A sample charging line 3 for charging a sample is connected between the valve 16 and valve 17, and a syringe 4 for injecting a charged particle suspension fluid to the sample charging line 3 is connected to the sample charging line 3. Furthermore, the sample charging line 3 is connected to a flow cell 5. The flow cell 5 is a cell which is capable of forming a flat flow by surrounding the particle suspension fluid flow in sheath fluid via a fluid dynamic effect. A sample fluid bottle 6 is connected to a waste chamber 14 through a sheath fluid chamber 7 and the flow cell 5. The flow cell is arranged medially to a strobe 8 and video camera 10, and an objective lens 9 is disposed between the flow cell 5 and the video camera 10.

The operation of the particle image sensing apparatus 21 is described below.

As shown in FIG. 2, when the valves 16 and 17 are open, the particle suspension fluid is suctioned from the suction pipette 1 by the pump 8, passes through the sample filter 2, and is introduced into the sample charging line 3 at the top of the flow cell 5. Coarse particle debris within the suspension fluid is removed by the sample filter 2, so as to prevent clogging of the small (narrow) flow path of the flow cell 5. Furthermore, the sample filter 2 also is effective for breaking up coarse aggregations.

The particle suspension fluid introduced into the charging line 3 is directed to the flow cell 5 by closing the valves 16 and 17 and operating the syringe 4 to eject the suspension fluid from the tip of an internal sample nozzle (not shown in the drawing). At the same time, sheath fluid is also fed from the sheath fluid bottle 6 to the flow cell 5 through the sheath fluid chamber 7 so as to surround the particle suspension fluid in the sheath fluid; the particle suspension fluid is constricted into a flat flow by flow dynamics within the flow cell 5, and is discharged through the waste chamber 14. The constricted flat flow of the suspension fluid is subjected to image sensing so as to capture a still image of the particles by the video camera 10 through the objective lens 9 by periodically irradiating the flow with pulsed light from the strobe 8.

The medium in which the particles are suspended may be selected from among suitable fluids in accordance with the particle characteristics (particle diameter and specific gravity).

Furthermore, it is desirable to change the viscosity and specific gravity of the sheath fluid in accordance with the characteristics of the suspension fluid, for example, the viscosity and specific gravity of the medium, so as to reliably flatten or narrowly constrict the flow of the suspension fluid. Although not shown in FIG. 2, a plurality of types of sheath fluid bottles may be provided, and a mechanism added for easily switching the type of sheath fluid used in accordance with the sample to be assayed.

Figure 3:
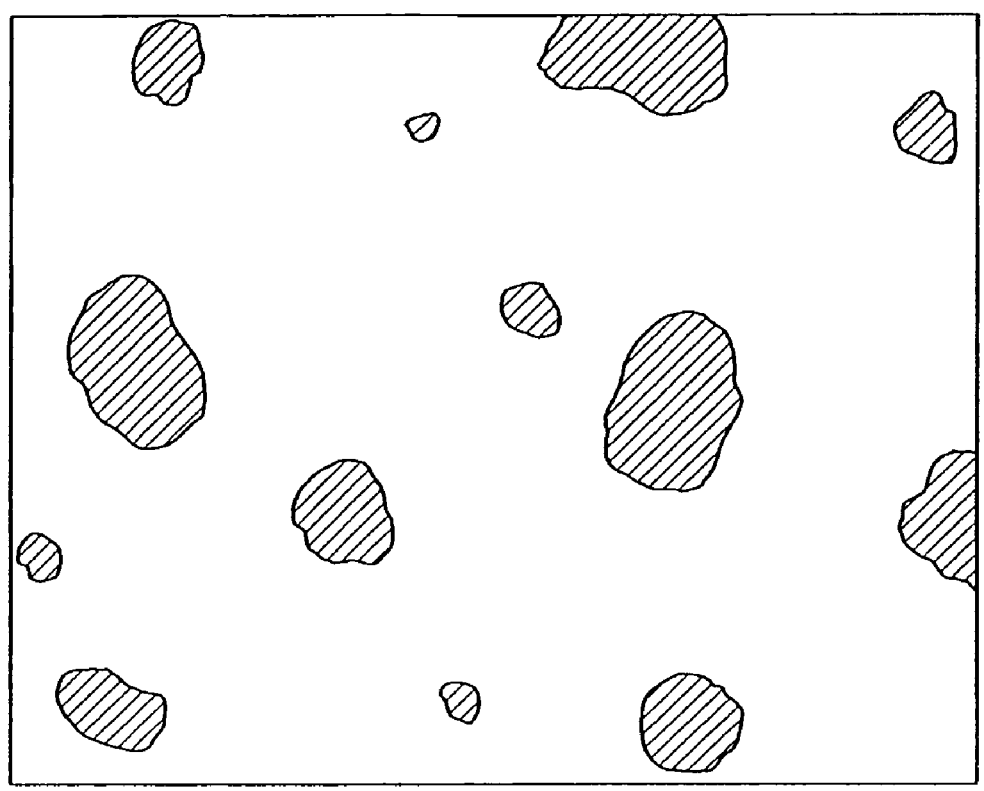
FIG. 3 shows an image in the first embodiment.

If the flattened surface of the suspension flow is photographed by the video camera 10, the particle image across the entire imaging area of the video camera 10 can be captured, and a plurality of particles can be photographed in a single image, as shown in FIG. 3. Furthermore, since the distance between the center of the imaged particles and the image sensing surface of the video camera 10 is substantially constant, a particle image is obtained which is normally focused regardless of the size of the particle.

Figure 4:
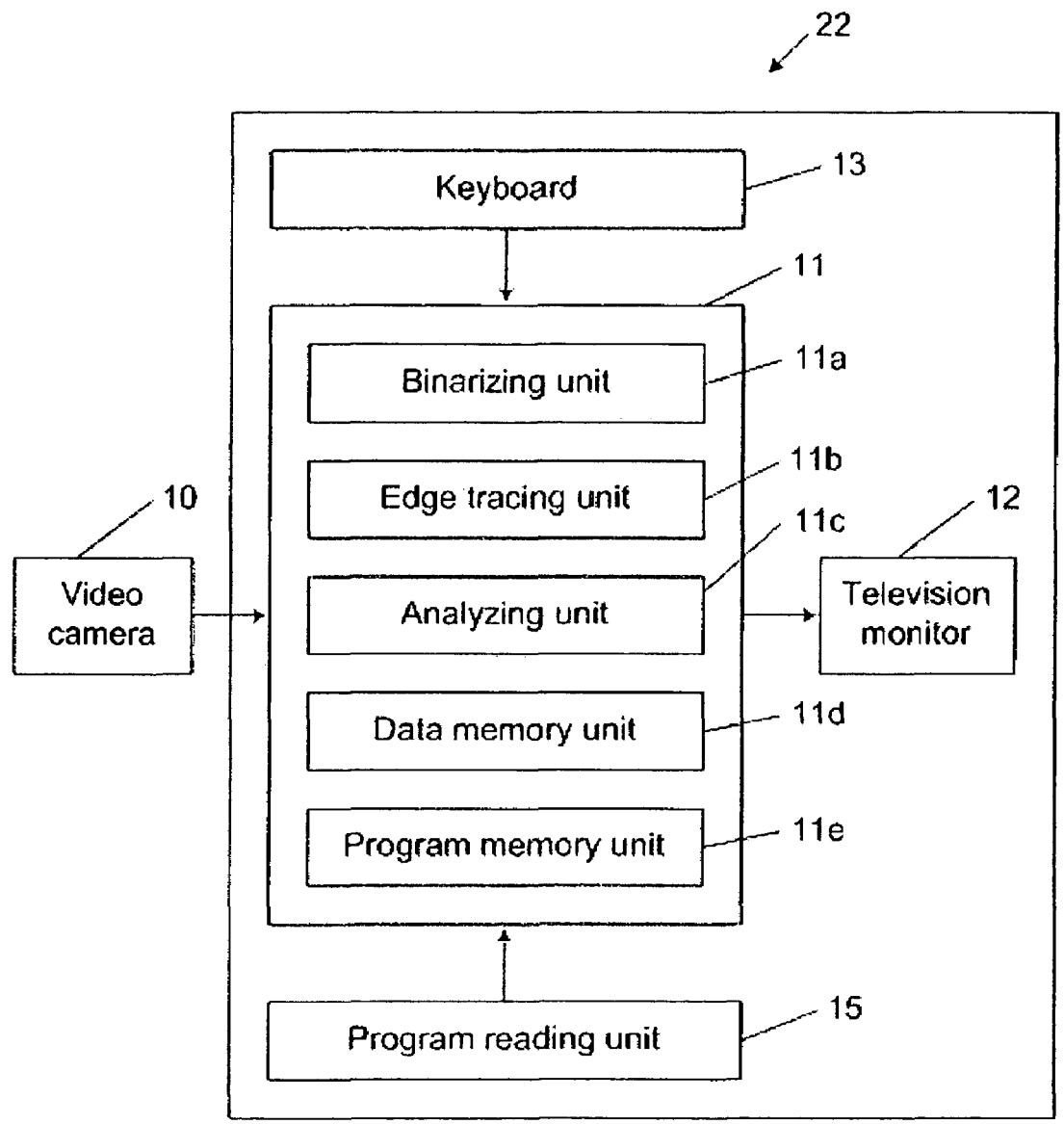
FIG. 4 is a block diagram showing the structure of a data analyzer in the first embodiment.

FIG. 4 is a block diagram showing the structure of the data analyzer 22. As shown in the drawing, the data analyzer 22 includes the particle image processing device 11 for processing the captured image transmitted from the video camera 10, television monitor 12 for displaying the analysis data and particle image output from the particle image processing device 11, keyboard 13 for performing operations and data input to the particle image processing device 11, and a program reading unit 15 for reading programs operating on the image processing device 11. The particle image processing device 11 is provided with a binarizing unit 11a for converting image signals from the video camera 10 to binary data, edge tracing unit 11b for edge tracing of binarized particle image data, analyzing unit 11c for analyzing data obtained by edge tracing, data memory unit 11d for storing image data and processing data and the like, and program memory unit 11d for storing particle image analyzing programs read from the program recording medium by the program reading unit 15. The program reading unit 15 is a CD-ROM drive, and the program recording medium is a CD-ROM. The data analyzer 22 processes image signals from the video camera 10 in accordance with processing conditions input from the keyboard 13, and the processing results are displayed on the television monitor 12. The particle image processing device 11 is a personal computer provided with a CPU, ROM, and RAM.

Figure 5:
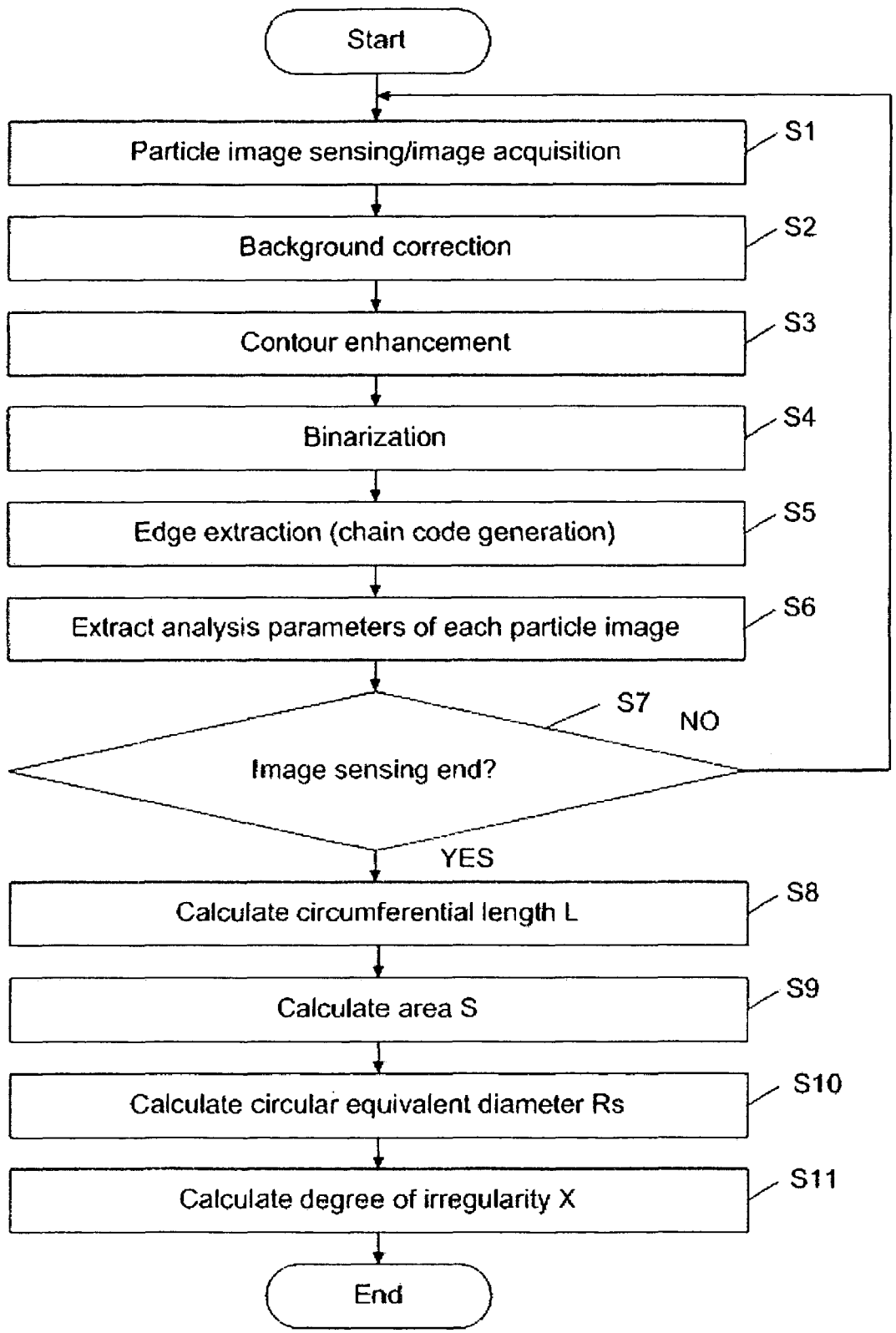
FIG. 5 is a flow chart showing an operation of the particle image analyzer of the first embodiment.

The image processing sequence in the data analyzer 22 is shown in the flow chart of FIG. 5. An image signal from the video camera 10 is received by the particle image processing device 11 and subjected to A/D conversion to obtain image data (step S1). Then, background correction is performed to correct the irregularities (shading) in the intensity of the light illuminating the suspension flow (step S2).

Specifically, image data obtained by light irradiation when particles are not flowing through the flow cell 5 is captured prior to the assay, and these image data and image data of the actual particle image sensing surface are compared in a well known process of image processing. Then, the contour of the particle image is subjected to a contour enhancement process as preprocessing to accurately extract the outline of the particle image (step S3). Specifically, generally well-known Laplacean enhancement processing is performed.

Figure 6:
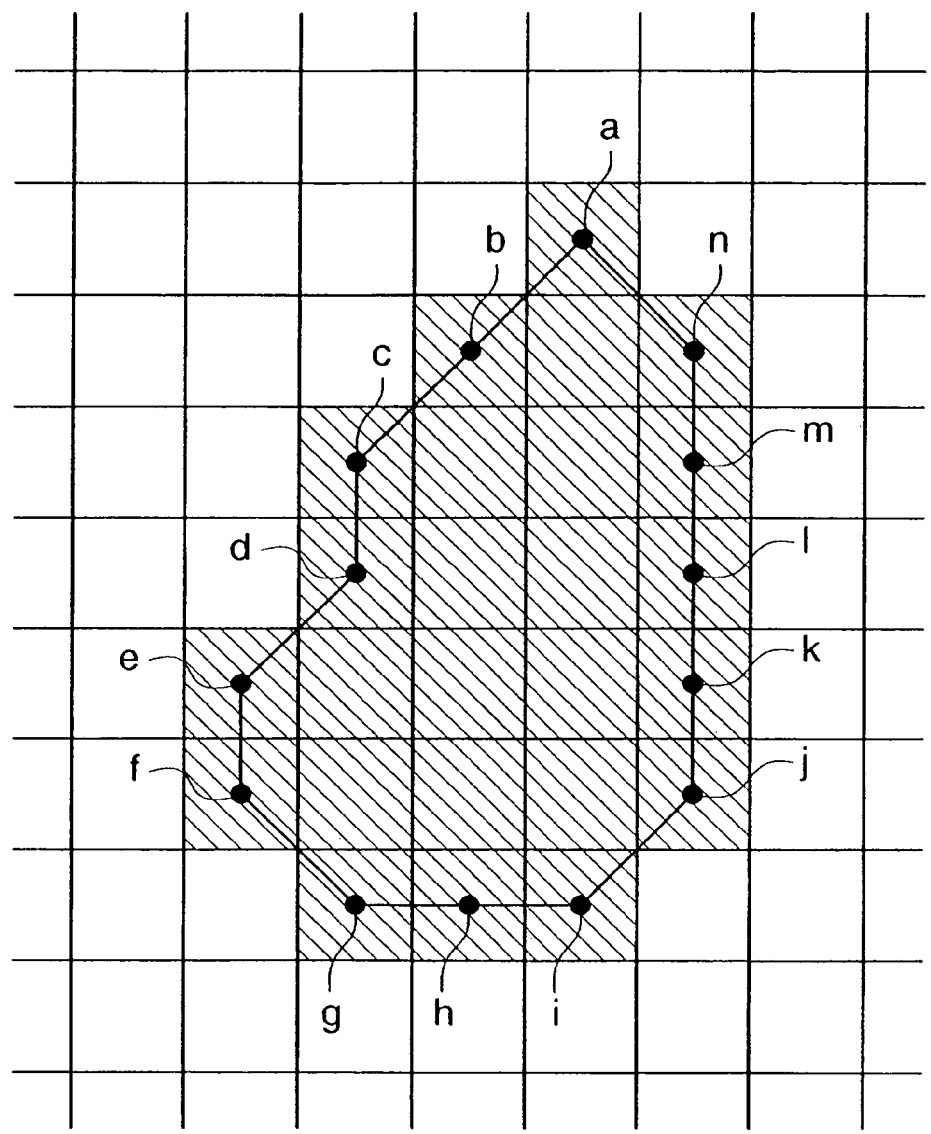
FIG. 6 shows a particle image in the first embodiment.

Next, image data meeting a suitable threshold level are binarized, and each particle image becomes a binary image as shown in FIG. 6 (step S4). Then, a determination is made as to whether or not the binarized particle image has edge points (contour pixels representing the outline), and information as to whether or not and in which direction the observed edge points have adjacent edge points, that is, a chain code, is generated (step S5). Thereafter, the particle image is subjected to edge tracing while referring to the chain code, and the area (total number of pixels) St, straight line count Et, diagonal line count Es, and corner count Cn of each particle image are determined as particle image analysis parameters (step S6).

In the description of the processes of steps S5 and S6 using FIG. 6, the center points a through n of the contour pixels (edge points) forming the outline of the particle image (shaded part of FIG. 6) are connected by straight lines; all the contour pixels are observed sequentially in a counterclockwise direction (or clockwise direction) from point a; the current target contour pixel is regarded as the first pixel when a straight line connects the current target contour pixel and the next target contour pixel in a vertical or horizontal direction; the current target contour pixel is regarded as the second pixel when a line connects the current target contour pixel and the next target contour in a diagonal direction; and the number of first and second pixels are counted.

The total number of first pixels is designated the straight line count Et, and the total number of second pixels is designated the diagonal line count Es.

In FIG. 6, when the line connecting a single target contour pixel and the adjacent contour pixels on both sides of the target contour pixel bends at the target contour pixel, the target contour pixel is regarded as an inflection point; and all contour pixels are individually observed and the number of inflection points counted. The total number of inflection points is designated the corner count Cn.

In the particle image shown in FIG. 6, the area St is the total number of pixels, which number 25; since the first pixels include points c, e, g, h, j, k, l, and m, the total number of first pixels Et is 8; since the second pixels include points a, b, d, f, i, and n, the total number of second pixels Es is 6; and since the inflection points include points a, c, d, e, f, g, i, j, and n, the total number of inflection points Cn is 9.

When the necessary image sensing process ends (step S7), first, the circumferential length L is calculated using the formula below based on the analysis parameters determined for each particle image (step S8).

$$L = 0.980 \times Et + 1.406 \times Es - 0.09 \times Cn \quad (1)$$

(where the unit length of one pixel is designated 1.)

Formula (1) is known as the Vossepoel Equation.

Next, the area S is calculated by the following formula (step S9).

$$S = St - 0.5L \quad (2)$$

(where the unit length of one pixel is designated 1.)

Then, the circular equivalent diameter Rs is calculated by the following formula (step S10).

$$Rs = a \times S^{1/2} \times k + b \quad (3)$$

In this formula, k represents the dimensions of one pixels, and a and b represent correction coefficients.

Then, the degree of irregularity X is calculated by the formula below (step S11).

$$X = Cn/L \quad (4)$$

The degree of irregularity X of the particle image shown in FIG. 6 is 0.58, because Cn=9, and L=15.5.

In this way, the circumferential length, area, circular equivalent diameter, and degree of irregularity X are displayed on the television monitor 12.

As described above, since the degree of irregularity can be obtained for each of a plurality of particle images without regard for the circumferential length, area, or circular equivalent diameter, the particle image can be statistically analyzed using these factors.

Second Embodiment

Figure 7:
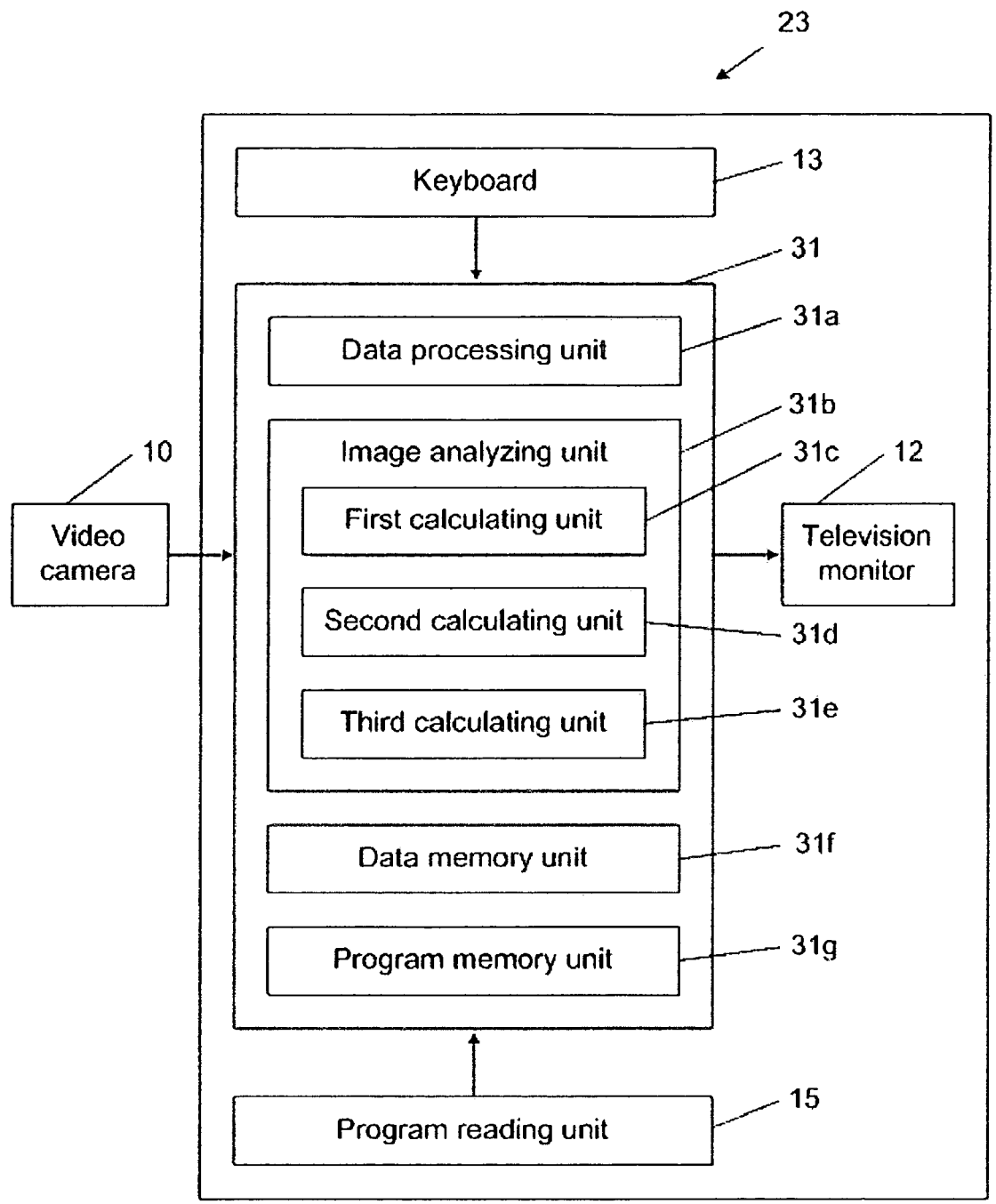
FIG. 7 is a block diagram showing a structure of a second embodiment of a data analyzer.

A second embodiment of the particle image analyzer of the present invention employs a data processing device 23, shown in FIG. 7, in place of the data analyzer 22 of the particle image analyzer of the first embodiment shown in FIG. 1, but in other respects has the same structure.

FIG. 7 is a block diagram showing the data analyzer 23. As shown in the drawing, the data analyzer 23 includes a particle image processing device 31 for processing captured images transmitted from the video camera 10, television monitor 12 for displaying analysis data and particle images output from the particle image processing device 31, keyboard 13 for performing operations and inputting data to the particle image processing device 31, and a program reading unit 15 for reading programs operating on the particle image processing device 31. The particle image processing device 31 is provided with a data processing unit 31a for processing image signals from the video camera 10, image analyzing unit 31b for analyzing the processed data, data memory unit 31f for storing image data and processed data and the like, program memory unit 31g for storing particle image analysis programs read from a program recording medium by the program reading unit 15. The program reading unit 15 is a CD-ROM drive, and the program recording medium is a CD-ROM. The image analyzing unit 31b includes a first calculating unit 31c for calculating the average value Ip of luminance of pixels representing the particle image, second calculating unit 31d for calculating the average value Ib of luminance of pixels representing the background image, and a third calculating unit 31e for calculating the light attenuation rate of the particle image from the values Ip and Ib. The data analyzer 23 processes image signals from the video camera 10 in accordance with processing conditions input from the keyboard 13, and displays the processing result on the television monitor 12. The particle image processing device 31 is a personal computer provided with a CPU, ROM, and RAM.

Figure 8:
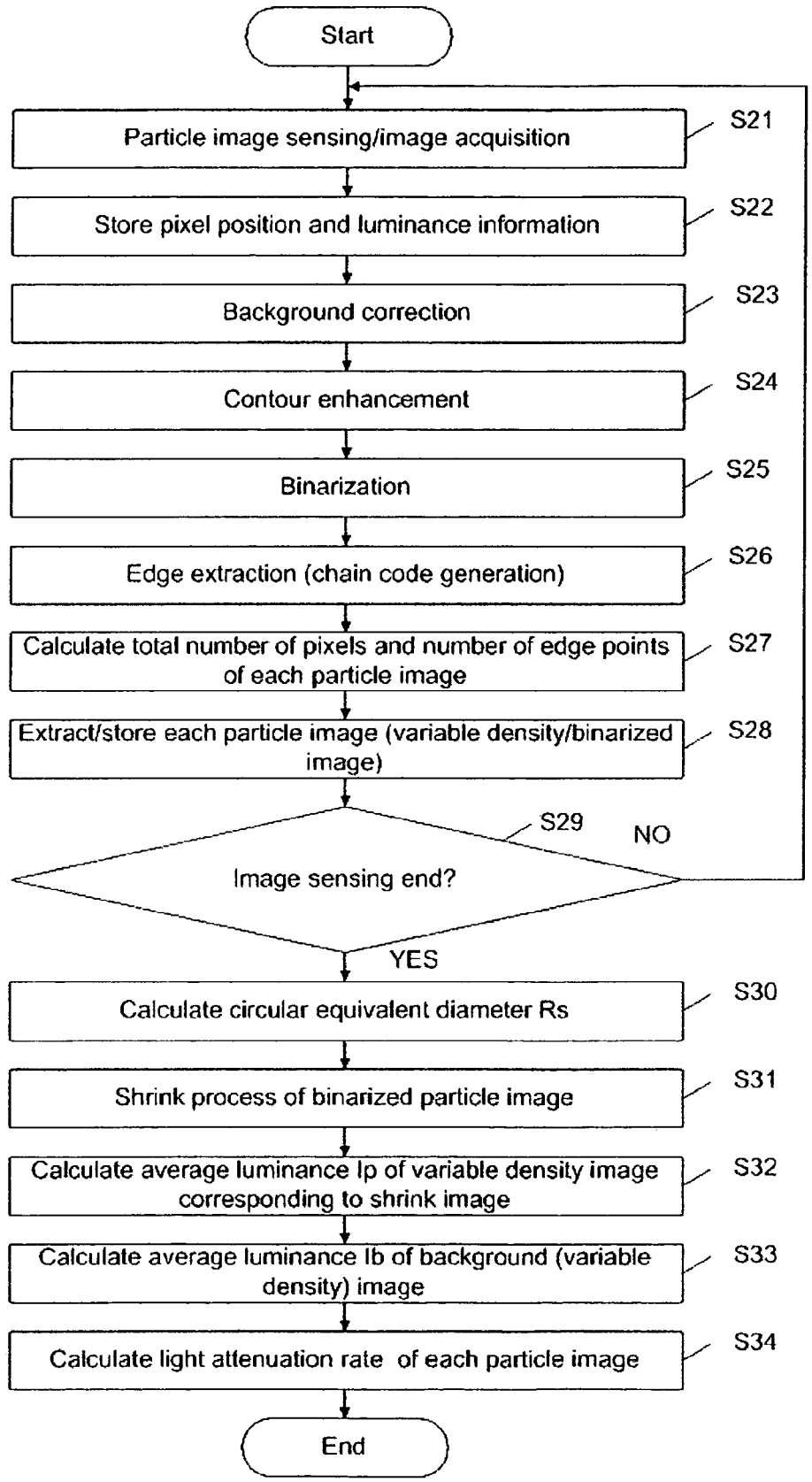
FIG. 8 is a flow chart showing an operation of a particle image analyzer of the second embodiment.

The image processing sequence performed in the data analyzer 23 is shown in the flow chart of FIG. 8. The image signal from the video camera 10 is received by the particle image processing device 11 and subjected to A/D conversion to obtain image data (step S21). Then, the luminance information and positions of the pixels in the image data are extracted and stored in the data memory unit 31f (step S22). Next, background correction is performed to correct the intensity unevenness (shading) of the illumination light on the suspension flow (step S23).

Specifically, image data obtained by irradiating with light the particle flow as it passes through the flow cell 5 are acquired prior to the assay, and these image data are compared to the actual image data of the particle image sensing surface in a generally well-known process of image processing. Then, the contour of the particle image is subjected to a contour enhancement process as preprocessing to accurately extract the outline of the particle image (step S24). Specifically, generally well-known Laplacean enhancement processing is performed.

Next, image data meeting a suitable threshold level are binarized, and each particle image becomes a binary image as shown in FIG. 6 (step S25). Then, a determination is made as to whether or not the binarized particle image has edge points (contour pixels representing the outline), and information as to whether or not and in which direction the observed edge points have adjacent edge points, that is, a chain code, is generated (step S26). Thereafter, the particle image is subjected to edge tracing while referring to the chain code, and the area (total number of pixels) St, straight line count Et, diagonal line count Es, and corner count Cn of each particle image are determined as particle image analysis parameters (step S27).

In the description of the processes of steps S26 and S27 using FIG. 6, the center points a through n of the contour pixels (edge points) forming the outline of the particle image (shaded part of FIG. 6) are connected by straight lines; all the contour pixels are observed sequentially in a counter-clockwise direction (or clockwise direction) from point a; the current target contour pixel is regarded as the first pixel when a straight line connects the current target contour pixel and the next target contour pixel in a vertical or horizontal direction; the current target contour pixel is regarded as the second pixel when a line connects the current target contour pixel and the next target contour in a diagonal direction; and the number of first and second pixels are counted.

The total number of first pixels is designated the straight line count Et, and the total number of second pixels is designated the diagonal line count Es.

In FIG. 6, when the line connecting a single target contour pixel and the adjacent contour pixels on both sides of the target contour pixel bends at the target contour pixel, the target contour pixel is regarded as an inflection point; and all contour pixels are individually observed and the number of inflection points counted. The total number of inflection points is designated the corner count Cn.

In the particle image shown in FIG. 6, the area St is the total number of pixels, which number 25; since the first pixels include points c, e, g, h, j, k, l, and m, the total number of first pixels Et is 8; since the second pixels include points a, b, d, f, i, and n, the total number of second pixels Es is 6; and since the inflection points include points a, c, d, e, f, g, i, j, and n, the total number of inflection points Cn is 9.

Then, each particle image (density/binarized image) is extracted, and the luminance of the pixels of each image is stored in the data memory unit 31f (step S28).

When the necessary image sensing process ends (step S29), the circular equivalent diameter Rs of each particle image is calculated as described below (step S30).

First, the circumferential length L is calculated using the formula below based on the analysis parameters determined for each particle image.

$$L = 0.980 \times Et + 1.406 \times Es - 0.091 \times Cn \quad (1)$$

(where the unit length of one pixel is designated 1.)

Formula (1) is known as the Vossepoel Equation.

Next, the area S is calculated by the following formula.

$$S = St - 0.5L \quad (2)$$

(where the unit length of one pixel is designated 1.)

Then, the circular equivalent diameter Rs is calculated by the following formula.

$$Rs = a \times S^{1/2} \times k + b \quad (3)$$

Then, the binarized image of each particle is subjected to processing to extract the center part of the particle image in a so-called shrink process (processing to eliminate the outer edges) (step S31), and the average luminance Ip is calculated from the luminance of variable density images corresponding to the shrink processed image (step S32). Since the pixels of the outer edge of the particle image easily affected by disturbances compared to the center pixels, the luminance information of the edge pixels are unstable and the luminance information reliability is low. Therefore, the average luminance Ip is calculated using the luminance of the center pixels of the particle image after the edges including the contour pixels have been removed.

The average luminance Ib is calculated from the luminance of the pixels of the background image stored in step S2 (step S33).

Then, the light attenuation rate α of each particle image is calculated using the following formula (step S34).

$$\alpha = (1/Rs) \times \log e(Ib/Ip) \quad (5)$$

When an offset value If is considered for Ib and Ip, Formula (5) can be written as follows.

$$\alpha = (1/Rs) \times \log e\{(Ib - If)/(Ip - If)\}$$

Formula (5) is based on the Lambert-Beer Law.

In this way the circumferential length, area, circular equivalent diameter, and light attenuation rate α are displayed on the television monitor 12.

As described above, since the light attenuation rate can be obtained for each of a plurality of particle images without regard for the circumferential length, area, or circular equivalent diameter, the particle image can be analyzed in detail by statistical processing using these factors.

The image analysis object in the first and second embodiments includes inorganic powders such as fine ceramics, pigments, cosmetic powders and the like, and organic powders such as food additives and the like, and may also include polycrystalline particles.

Although a strobe is used as a pulse light source in the first and second embodiments, a pulse laser light source also may be used.

Although the flow cell is disposed medially to the strobe and video camera in the first and second embodiments, insofar as the particle suspension fluid forms a flat flow in the flow cell, it is desirable that the strobe is disposed so as to irradiate the entire flat surface of the particle suspension fluid, and the video camera is disposed on the optical axis of the strobe.

Although a CD-ROM is used as the recording medium in the first and second embodiments, magnetic tapes and cassette tapes, magnetic disks such as floppy (registered trademark) disks and hard disks, optical disks such as CD-MO/MD/DVD and the like, IC cards (including memory cards) and optical cards, or semiconductor memories such as ROM, EPROM, EEPROM, and flash ROM and the like also may be used.

Furthermore, the particle image analyzer may have a system structure capable of connecting to a communication network including the internet, and the recording medium may be a recording medium which fluidly maintains programs so as to download programs from the communication network. The download programs may be stored beforehand in the particle image processing device.

It is therefore intended that the foregoing detailed description be regarded as illustrative rather than limiting, and that it be understood that it is the following claims, including all equivalents, that are intended to define the spirit and scope of this invention.

The invention claimed is:

1. A method for processing particle images comprising the steps of:
   receiving image information obtained by capturing an image of a particle;
   determining the circumferential length and number of inflection points in the contour of a particle image based on the received image information; and
   calculating the degree of irregularity of the particle based on the determined circumferential length and number of inflection points.

2. The method for processing particle images of claim 1, wherein the determining step comprises the steps of:
   determining a chain code tracing the contour pixels forming the outline of the particle image; and
   determining the circumferential length of the particle and the number of inflection points of the contour of the particle image using the determined chain code.

3. The method for processing particle images of claim 2, wherein the step of determining a chain code determines a chain code tracing the pixel center of the contour pixels.

4. The method for processing particle images of claim 1, wherein the degree of irregularity is the ratio of the number of inflection points and the circumferential length.

5. A particle image processing apparatus comprising:
   an image information receiving means for receiving image information obtained by capturing an image of a particle; and
   an analyzing means for determining a circumferential length and number of inflection points in the contour of a particle image based on the received image information, and determining the degree of irregularity of a particle based on the determined circumferential length and number of inflection points.

6. The particle image processing apparatus of claim 5, wherein the analyzing means comprises a binarizing unit for binarizing image information received by the image information receiving means; edge tracing unit for generating a chain code tracing the contour pixels forming the outline of a particle image in the binarized image information and extracting the number of inflection points based on the generated chain code; and calculating means for determining the circumferential length based on the number of extracted inflection points and calculating the degree of irregularity of a particle based on the determined circumferential length and the number of inflection points.

7. The particle image processing apparatus of claim 6, wherein the edge tracing unit determines the chain code for tracing the pixel center of the contour pixels.

8. The particle image processing apparatus of claim 6, wherein the calculating means determines the degree of irregularity from the ratio of the number of inflection points and the circumferential length.

9. The particle image processing apparatus of claim 6, wherein the analyzing means determines the circular equivalent diameter based on the binarized image information.

10. A particle image analyzing apparatus comprising:
    a flow cell for forming a suspension fluid flow containing particles;
    a light source for irradiating the suspension flow with light;
    an image sensing unit for capturing an image of a particle irradiated by light and generating image information; and
    an analyzing means for generating image data based on the image information, and calculating the degree of irregularity of the particle based on the circumferential length and number of inflection points of the contour of the particle image in the image data.

11. A computer readable medium storing a particle image processing program comprising the computer-executable steps of:
    receiving image information obtained by capturing a particle image;
    determining the circumferential length and number of inflection points of the contour of a particle image based on the received image information; and
    calculating the degree of irregularity of a particle based on the circumferential length and number of inflection points of the contour of a determined particle image.

12. The particle image processing program product of claim 11, wherein the step of calculating the degree of irregularity of a particle comprises steps:
    binarizing the received image information;
    generating a chain code for tracing the contour pixels which form the outline of the particle image in the binarized image data;
    extracting the number of inflection points based on the generated chain code; and
    a step of determining the circumferential length based on the number of extracted inflection points.

* * * * *